United States Patent

Sherman et al.

[11] 4,329,160
[45] May 11, 1982

[54] SUPPRESSION OF COS FORMATION IN MOLECULAR SIEVE PURIFICATION OF HYDROCARBON GAS STREAMS

[75] Inventors: John D. Sherman, Chappaqua, N.Y.; Arthur T. Katsaros, Macungie, Pa.

[73] Assignee: Union Carbide Corporation, Danbury, Conn.

[21] Appl. No.: 935,757

[22] Filed: Aug. 22, 1978

Related U.S. Application Data

[63] Continuation-in-part of Ser. No. 836,001, Sep. 23, 1977, abandoned, which is a continuation of Ser. No. 486,638, Jul. 8, 1974, abandoned.

[51] Int. Cl.³ .............................................. B01D 53/04
[52] U.S. Cl. ......................................... 55/62; 55/73; 55/75
[58] Field of Search .................... 55/33, 68, 71, 73, 74, 55/75, 62

[56] References Cited

U.S. PATENT DOCUMENTS

| | | | |
|---|---|---|---|
| 2,996,558 | 8/1961 | Feldbauer, Jr. | 55/75 X |
| 3,061,992 | 11/1962 | Russell | 55/75 X |
| 3,078,634 | 2/1963 | Milton | 55/75 X |
| 3,078,640 | 2/1963 | Milton | 55/73 |
| 3,078,641 | 2/1963 | Milton | 55/73 |
| 3,416,293 | 12/1968 | Alexander | 55/74 X |
| 3,470,677 | 10/1969 | Eck et al. | 55/73 |
| 3,660,967 | 5/1972 | Collins et al. | 55/73 |
| 3,751,878 | 8/1973 | Collins | 55/75 X |
| 3,808,773 | 5/1974 | Reyhing et al. | 55/73 X |

Primary Examiner—Robert H. Spitzer
Attorney, Agent, or Firm—Richard G. Miller

[57] ABSTRACT

In the process for purifying hydrocarbon gas streams containing hydrogen sulfide and carbon dioxide as impurities by contact thereof with zeolitic molecular sieve adsorbents to selectively adsorb the impurities, the formation of carbonyl sulfide by the zeolite catalyzed reaction of $H_2S$ with $CO_2$ is greatly suppressed by employing as the selective adsorbent certain cation forms of molecular sieve zeolites which contain from 0.7 to 3 weight percent adsorbed water.

2 Claims, 1 Drawing Figure

U.S. Patent May 11, 1982 4,329,160
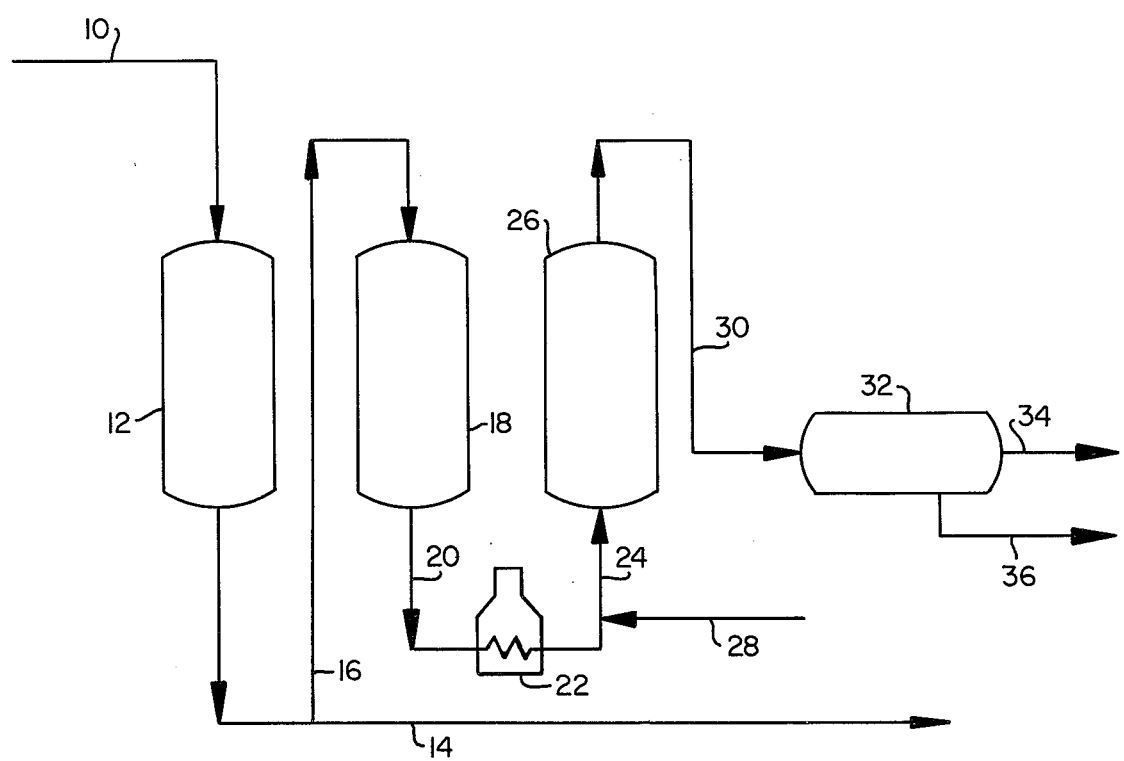

SUPPRESSION OF COS FORMATION IN MOLECULAR SIEVE PURIFICATION OF HYDROCARBON GAS STREAMS

RELATED APPLICATIONS

This application is a continuation-in-part of our prior application Ser. No. 836,001 filed Sept. 23, 1977 and now abandoned, which is in turn a continuation of application Ser. No. 486,638, filed July 8, 1974 and now abandoned.

The present invention relates in general to the purification of hydrocarbon gas streams containing as impurities $H_2S$ and $CO_2$, and more particularly to process whereby $H_2S$ is selectively adsorbed from such hydrocarbon gas streams using zeolitic molecular sieves having minimal catalytic activity with respect to reaction between $H_2S$ and $CO_2$ to form COS.

The gas phase treatments of hydrocarbon feedstocks, particularly natural gas, to remove $H_2S$ and other impurities by selective adsorption and absorption techniques is well known. Natural gas, for example, commonly contains water, hydrogen sulfide, carbon dioxide, plus other sulfur compounds and heavier hydrocarbons in various concentrations depending upon its source. The end use of the natural gas dictates which impurities must be removed and the extent of that removal. When the gas is to be transported by pipeline, there are specifications for its water and corrosive sulfur, as hydrogen sulfide, contents. Transmission and some other end uses do not require removal of carbon dioxide except in those instances where a minimum heating value needs to be met. Natural gas feed to a liquefaction unit requires much more thorough clean-up to protect against solids formation by water and carbon dioxide in the cryogenic equipment.

The selective adsorption character of molecular sieve has been quite ideal for these purifications for the reason that the order of adsorption selectivity is: $H_2O > H_2S > CO_2 > CH_4$. Thus when crude natural gas is passed through a molecular sieve adsorbent bed, the impurities adsorb in zones and it is possible to adsorb only the water, or water and $H_2S$, or $H_2O$, $H_2S$ and $CO_2$ to any desired extent.

It has been found, however, that when both $H_2S$ and $CO_2$ are present in the feedstock, COS is frequently present in the product gas, i.e., after treatment in a molecular sieve purification unit, in higher concentrations than in the feed. This is apparently due to the fact that the molecular sieve serves as a catalyst for the reaction

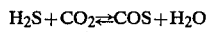

$$H_2S + CO_2 \rightleftharpoons COS + H_2O$$

and also due to the fact that the COS, once produced in the adsorption bed is not retained therein as an impurity adsorbate because of its low polarity and low boiling point compared with the same properties of the other impurity molecules present.

Accordingly, it is the principal object of the present invention to provide a means to suppress the formation of COS when sweetening hydrocarbon gas streams containing both $H_2S$ and $CO_2$ using molecular sieve adsorbents.

This object, we have found, is accomplished in the cyclic process comprising the steps of the cyclic process comprising the steps of (a) an adsorption purification stroke wherein a hydrocarbon stream containing $H_2S$ and $CO_2$ is contacted in the vapor phase at a temperature of from 60° F. to 120° F. with a zeolitic molecular sieve adsorbent in a fixed bed to selectively adsorb $H_2S$ and a hydrocarbon product is recovered which is substantially free of $H_2S$; (b) a purge desorption stroke wherein a portion of the substantially $H_2S$—free hydrocarbon product recovered in step (a) is heated to above 120° F. and passed countercurrently through the adsorption bed to desorb substantially all of the adsorbate molecules selectively adsorbed in step (a) and flush same from the bed; (c) a cool-down stroke wherein the bed is cooled to below 120° F. by the cocurrent purge therethrough of a portion of the substantially $H_2$-free hydrocarbon recovered in step (a) at a temperature of from 60° F. to 120° F.; the improvement which comprises utilizing as the said molecular sieve adsorbent a crystalline zeolite having a pore diameter of at least 5 Angstroms, at least 45 percent of the framework aluminum atoms thereof being associated with at least one species of alkaline earth metal cation having an atomic number of less than 56, and injecting into said hydrocarbon stream prior to passage through the bed in step (b) a sufficient amount of water vapor to import a substantially uniform adsorbed water loading of from 0.7 to 3.0 weight percent to the molecular sieve adsorbent.

Although the preferred feedstock for treatment in accordance with the present process is $CO_2$-containing sour natural gas, any hydrocarbon of mixture of hydrocarbons containing $H_2S$ and $CO_2$ which is in the vapor state at a temperature within the range of 60° F. to 120° F. and a pressure of from 200 to 1200 psia and which is less strongly adsorbed than $H_2S$ is suitably treated. The preferred natural gas feedstock contains, in addition to methane, water in any concentration up to saturation, up to 5 mole percent $H_2S$, from 0.5 to 55 mole percent $CO_2$ and not more than 25 mole percent hydrocarbons having more than one carbon atom. Commonly such hydrocarbon feedstocks will also contain organic sulfur compounds such as mercaptans.

The drawing is a schematic flow diagram showing a three bed process system suitably employed in the practice of the present process.

The molecular sieve zeolite adsorbent can be any naturally occurring or synthetic crystalline zeolite which contains at least 45 equivalent percent beryllium, magnesium, calcium, or strontium cations or mixtures of any two or more of such cations and which has in this cation form a pore diameter of at least 5 Angstroms. The calcium cation forms of zeolite A and zeolite X as defined in U.S. Pat. No. 2,882,243 and U.S. Pat. No. 2,883,244 respectively, have been found to have especially low catalytic activity with respect to the reaction of $H_2S$ and $CO_2$ and are particularly preferred in the present process. Other suitable zeolites include the calcium cation forms of mordenite, chabazite, faujasite and zeolites Y disclosed in U.S. Pat. No. 3,130,007; zeolite T disclosed in U.S. Pat. No. 2,950,952; zeolite L disclosed in U.S. Pat. No. 3,216,789; and zeolite omega disclosed in pending U.S. application Ser. No. 655,318, filed July 24, 1967.

The required water loading on the zeolite adsorbent is readily attained by any conventional means. In cyclic continuous operation in which an adsorbent bed is periodically desorbed by means of a hot purge gas, commonly a portion of the purified product gas, it is convenient to inject water vapor into that purge gas stream in appropriate amount such that after desorption and cool-down of the bed is complete, the requisite water loading remains on the bed.

The following example is illustrative of the present process:

EXAMPLE 1

(a) With reference to the drawing, a natural gas feedstock having the following composition was employed in the process:

| | | |
|---|---|---|
| $CH_4$ | 95. | mole % |
| $H_2O$ | .106 | " |
| $CO_2$ | 3. | " |
| $H_2S$ | .006 | " |

In the drawing it is to be understood that each of the three adsorbent beds shown are equivalent and each in turn would, in conventional operation, undergo the steps of adsorption, hot purge desorption and cool-down in preparation for the next cycle of the same three steps. For simplicity, the various valves, manifolds, pumps, etc. ordinarily used in this conventional three-bed type of operation have been omitted. The drawing shows the simultaneous operation in each of the three beds.

The aforesaid feedstock is fed at a pressure of 1045 psia through line 10 to adsorber 12 which contains as the adsorbent zeolite A having 80 equivalent percent calcium cations and 20 equivalent percent sodium cations and containing 2.6 weight-% adsorbed $H_2O$. Adsorber 12 is operated during this adsorption step at 92° F. The effluent from the adsorber 12 is essentially pure methane. In due course an adsorption front for each of the components $H_2O$, $H_2S$ and $CO_2$ are formed in the adsorber with $H_2O$ front being closest to the ingress end of the bed and the $CO_2$ front being nearest the egress end of the bed. Since in this embodiment it is the purpose to remove only the $H_2S$, the $CO_2$ front is permitted to break through the egress end of the adsorber and commingle with the product methane which is in the main removed from the system through line 14. A portion of the product methane is continuously passed through line 16 to the top of adsorber 18 which at the beginning of the adsorption stroke in adsorber 12 had just finished being hot purge desorbed and contains essentially $H_2S$-free product methane. The adsorber is at a temperature of 500° F. The purified methane entering adsorber 18 is at a temperature of 92° F. and in its passage through adsorber 18 cools that adsorber until a temperature of 125° F. is reached. The thus heated gas leaving bed 18 is passed through line 20, furnace 22 where the temperature is raised to 550° F., and line 24 into adsorber 26 which at the beginning of the adsorption fill stroke in adsorber 12 has just completed a downward adsorption fill stroke using feedstock of the same composition as is currently being introduced through line 10. The heated purge gas from furnace 22 is injected with water through line 28 to raise the water vapor content to 0.185 mole percent. The desorbate stream from adsorber 26 which contains the $H_2O$ and $H_2S$ previously adsorbed is fed through line 30 to sulfur recovery unit 32. Stack gases are passed from the system through line 34 and sulfur collected from line 36. The COS content of the product methane leaving the system through line 14 is less than 8 ppm.

(b) Using the same procedure, feedstock and apparatus as set forth in part (a) above, except that the zeolite adsorbent in adsorber 12 contained less than 0.7 weight-% adsorbed $H_2O$, the COS content of the product methane leaving the system through line 14 is about 45 ppm.

What is claimed is:

1. A cyclic process comprising the steps of:
   (a) an adsorption purification stroke wherein a hydrocarbon stream containing $H_2S$ and $CO_2$ is contacted in the vapor phase at a temperature of from 60° F. to 120° F. with a molecular sieve adsorbent in a fixed bed to selectively adsorb $H_2S$ and a hydrocarbon product is recovered which is substantially free of $H_2S$;
   (b) a purge desorption stroke wherein a portion of the substantially $H_2S$-free hydrocarbon product recovered in step (a) is heated to above 120° F. and passed countercurrently through the adsorption bed to desorb substantially all of the adsorbate molecules selectively adsorbed in step (a) and flush same from the bed;
   (c) a cool-down stroke wherein the bed is cooled to below 120° F. by the cocurrent purge therethrough of a portion of the substantially $H_2S$-free hydrocarbon recovered in step (a) at a temperature of from 60° F. to 120° F.;

the improvement which comprises utilizing as the said molecular sieve adsorbent a crystalline zeolite having a pore diameter of at least 5 Angstroms, at least 45 percent of the framework aluminum atoms thereof being associated with at least one species of alkaline earth metal cation having an atomic number of less than 56, and injecting into said hydrocarbon stream prior to passage through the bed in step (b) a sufficient amount of water vapor to impart a substantially uniform adsorbed water loading of from 0.7 to 3.0 weight percent to the molecular sieve adsorbent.

2. Process according to claim 1 wherein the hydrocarbon of the stream being treated is methane containing not greater than 5 mole percent $H_2S$ from 0.5 to 55 mole percent carbon dioxide, and the molecular sieve adsorbent is the calcium cation form of zeolite A having at least 45 equivalent percent calcium cations.

* * * * *